(12) United States Patent
Keshavmurthy

(10) Patent No.: US 6,266,138 B1
(45) Date of Patent: Jul. 24, 2001

(54) SYSTEM AND METHOD FOR DETECTING DEFECTS IN A SURFACE OF A WORKPIECE

(75) Inventor: Shyam P. Keshavmurthy, Canton, MI (US)

(73) Assignee: Perceptron, Inc., Plymouth, MI (US)

( * ) Notice: Subject to any disclaimer, the term of this patent is extended or adjusted under 35 U.S.C. 154(b) by 0 days.

(21) Appl. No.: 09/415,930

(22) Filed: Oct. 12, 1999

(51) Int. Cl.⁷ .................................................. G01N 21/00
(52) U.S. Cl. ...................... 356/237.2; 356/371; 356/394
(58) Field of Search ............................. 356/237.2, 237.1, 356/371, 445, 446, 448, 394; 382/141, 168, 257, 107; 250/462.1, 463.1; 348/128, 92, 94, 125, 126

(56) References Cited

U.S. PATENT DOCUMENTS

| | | |
|---|---|---|
| 4,918,321 | 4/1990 | Klenk et al. . |
| 5,237,404 | 8/1993 | Tanaka et al. . |
| 5,331,169 * | 7/1994 | Tanaka et al. ..................... 356/237.2 |
| 5,367,378 | 11/1994 | Harding et al. . |
| 5,379,347 * | 1/1995 | Kato et al. ............................... 382/8 |
| 5,389,794 | 2/1995 | Allen et al. . |
| 5,414,518 * | 5/1995 | Yazejian ................................ 356/371 |
| 5,461,474 | 10/1995 | Yoshii et al. . |
| 5,583,640 * | 12/1996 | Ventura et al. ....................... 356/371 |
| 5,642,198 | 6/1997 | Long et al. . |
| 5,726,705 | 3/1998 | Imanishi et al. . |
| 5,734,742 | 3/1998 | Asaeda et al. . |

OTHER PUBLICATIONS

Tonda, Sylvie G. Réfrégier, Philippe; Three–dimensional attitude estimation and tracking with linear normalized optimal filtering; Optical Engineering, vol. 36 No. 4, Apr. 1997.

Tsai, Roger Y.; Versatile Camera Calibration Technique for High–Accuracy 3D Machine Vision Metrology Using Off–the–Shelf TV Cameras and Lenses; IEEE Journal Robotics and Automation, vol. RA–3, No. 4, Aug. 1987.

* cited by examiner

*Primary Examiner*—Hoa Q. Pham
(74) *Attorney, Agent, or Firm*—Harness, Dickey & Pierce, P.L.C.

(57) ABSTRACT

A surface inspection system is provided for detecting defects on a surface of a workpiece. The surface inspection system includes a diffused light source for emitting an elongated line of light onto the surface of the workpiece, a movable member for translating the workpiece in relation to the light source, an imaging device positioned at a vantage point such that the line of light is within its field of observation for capturing two or more sets of image data representative of a portion of the surface of the workpiece, and a data structure for storing model data, where the model data is indicative of the spatial relationship between the surface of the workpiece and the observation plane of the imaging device. The surface inspection system further includes an anomaly detection module adapted to receive the image data from the imaging device and for identifying at least one potential surface defect in the image data, and a defect tracking module connected to the data structure and the anomaly detection module for tracking the potential surface defect from the first set of image data to the second set of image data by using said model data, thereby assessing if the potential surface defect constitutes a defect in the surface of the workpiece.

28 Claims, 10 Drawing Sheets

SYSTEM AND METHOD FOR DETECTING DEFECTS IN A SURFACE OF A WORKPIECE

BACKGROUND AND SUMMARY OF THE INVENTION

The present invention relates generally to an automated surface inspection system and, more particularly, a system and method for detecting defects on a painted surface of a workpiece.

Demand for higher quality has pressed manufacturers of mass produced articles, such as automotive vehicles, to employ automated manufacturing techniques that were unheard of when assembly line manufacturing was first conceived. Today, robotic equipment is used to assemble, weld, finish, gauge and test manufactured articles with a much higher degree of quality and precision than has been heretofore possible. Computer-aided manufacturing techniques allow designers to graphically conceptualize and design a new product on a computer workstation and the automated manufacturing process ensures that the design is faithfully carried out precisely according to specification.

Quality control is also an important component of the automated manufacturing process. For instance, rather than employing human inspectors, automated surface inspection systems are used to perform repetitive visual inspection of a workpiece in order to detect flaws in the surface of a workpiece.

An imaging device is typically used in an automated surface inspection system to capture frames of image data representative of a portion of the surface of the workpiece. To determine what constitutes a surface defect, the surface inspection system compares the location of a potential surface defect from frame to frame. In the conventional case, the surface inspection system assumes that the inspection surface is substantially planar, and thus the potential surface defect is moving at the same or proportional rate (in relation to the imaging device) at which the workpiece is being translated by the movable member. However, for contoured inspection surfaces, the potential surface defect does not travel at the same rate in relation to the imaging device as the velocity of the movable member. As a result, conventional surface inspection systems are unable to accurately compare the location of a potential defect between frames, and thus may be unable to identify surface defects in contoured inspection surfaces.

Therefore, it is desirable to provide an automated system and method for detecting defects in a contoured surface of a workpiece. To the extent that the inspection surface is painted, it is also desirable that the surface inspection system distinguish surface flaws caused by dirt, pinholes or scratches from the surface roughness of the paint (i.e., "orange peel") on the workpiece. It would further be advantageous if such a system were able to characterize the defects by size so that only those body parts having defects larger than a certain threshold size would need to be rejected by the inspection process.

SUMMARY OF THE INVENTION

In accordance with the present invention, a surface inspection system is provided for detecting defects on a surface of a workpiece. The surface inspection system includes a diffused light source for emitting an elongated line of light onto the surface of the workpiece, a movable member for translating the workpiece in relation to the light source, an imaging device positioned at a vantage point such that the line of light is within its field of observation for capturing two or more sets of image data representative of a portion of the surface of the workpiece, and a data structure for storing model data which is indicative of the spatial relationship between the surface of the workpiece and the observation plane of the imaging device. The surface inspection system further includes an anomaly detection module for identifying at least one potential surface defect in the image data and a defect tracking module connected to the data structure and the anomaly detection module for tracking the potential surface defect from the first set of image data to the second set of image data, thereby assessing if the potential surface defect constitutes a defect in the surface of the workpiece.

For a more complete understanding of the invention, its objects and advantages, reference may be had to the following specification and to the accompanying drawings.

DESCRIPTION OF THE PREFERRED EMBODIMENT

Figure 1:
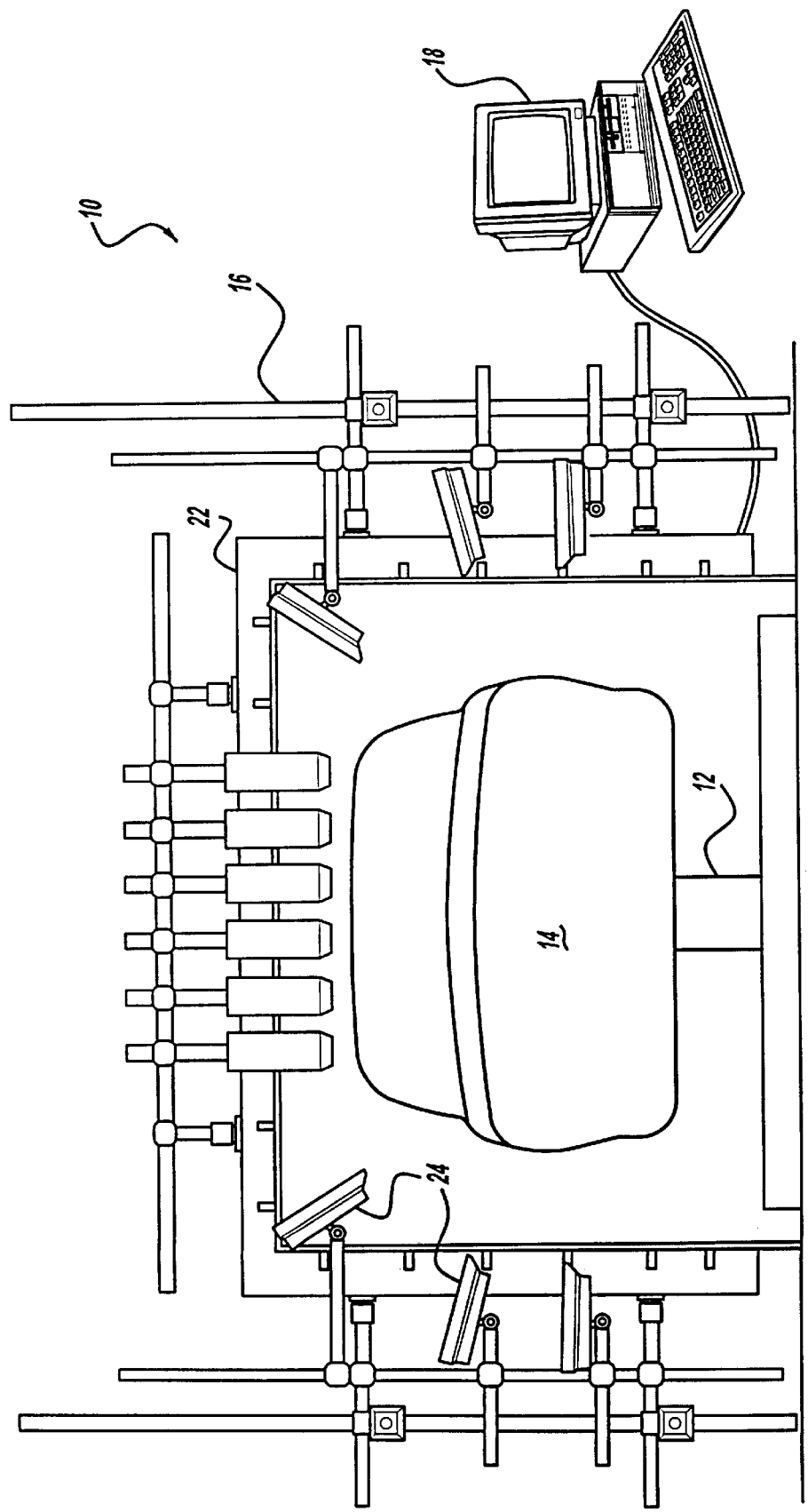
FIG. 1 is a perspective view of a surface inspection station on an automotive assembly line in accordance with the present invention.

An exemplary surface inspection system of the type commonly employed in vehicle assembly lines is shown in FIG. 1. The surface inspection system 10 includes a conveyer system 12 for carrying vehicle bodies 14 through various assembly stations on the assembly line. A mounting frame 16 surrounds the conveyor system 12 and provides a mounting position for at least two light sources 22. In addition, the mounting frame 16 provides a plurality of other mounting positions for a series of imaging devices 22. Communication cables, which are not specifically shown in FIG. 1, couple the light sources 22 and the imaging devices 24 to one or more computing devices 18. Although the invention is not limited to automotive applications, an exemplary use for the surface inspection system of the present invention would be in an automotive assembly plant.

Figure 2:
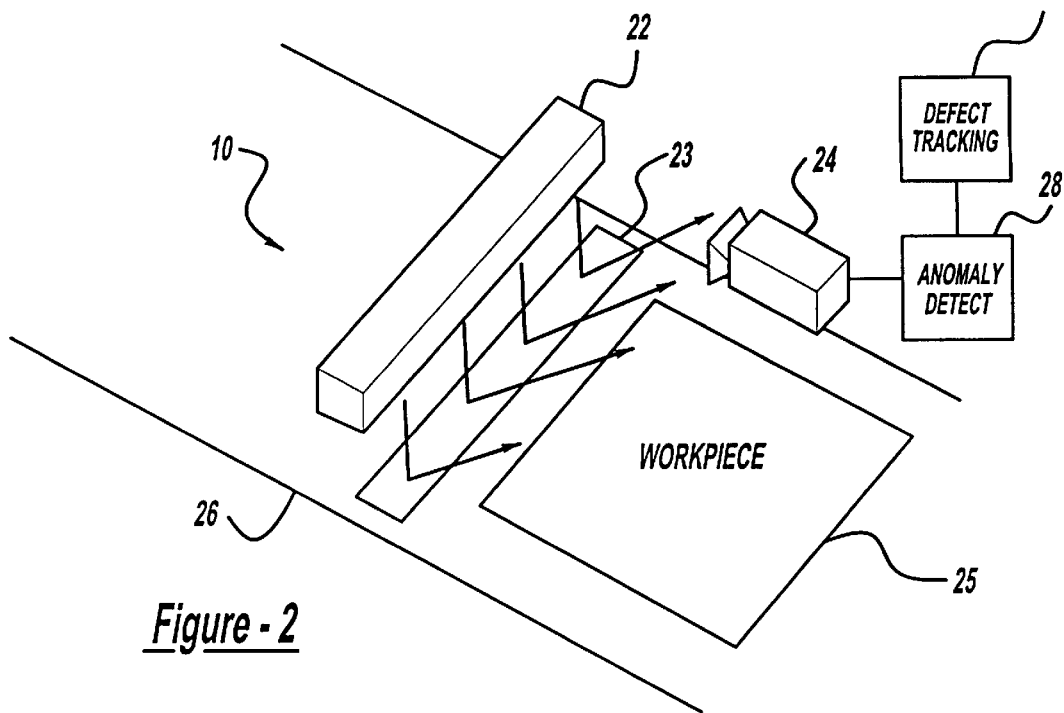
FIG. 2 is a block diagram of the basic components of the surface inspection system of the present invention.

FIG. 2 illustrates the basic components associated with the surface inspection system 10 in accordance with the present invention. The surface inspection system 10 generally includes two diffused light sources 22, one or more imaging devices 24, a movable member 26, an anomaly detection subsystem 28, and a defect tracking subsystem 30.

Two light sources 22 are used to emit two elongated lines of light 23 onto the surface of a workpiece 25. Preferably, each light source 22 is a fluorescent lamp diffused through a thin sheet of diffusing film. An exemplary light source is manufactured by Plastic Films Company. It is also envisioned that a baffle (not shown) may be positioned between each of the light sources 22. Although two light sources are presently preferred, this is not intended as a limitation of the invention. On the contrary, one or more light sources may be suitably used.

At least one imaging device 24 is used to capture image data representative of a portion of the surface of the workpiece. The imaging device 24 is positionable at a vantage point such that the line of light 23 is within the device's field of observation. It should be noted that the length of the light source 22 is such that the field of observation of the imaging device 24 is fully illuminated by the light source 22. An exemplary imaging device 24 may be one of a variety of CCD cameras manufactured by Pulnix Corporation. While the following description is provided with reference to one imaging device, it is readily understood that a plurality of imaging devices may be used to inspect the same or different portions of the surface of the workpiece.

Generally, the intensity of light source along with the imaging device and its lens setting are chosen so that surface defects such as dirt, craters, solvent pops, and scratches create contrast in the captured image which is greater than the surface roughness of the paint on the workpiece (commonly referred to as "orange peel"). The light intensity gradient from the elongated lines of light is such that it provides a means for emphasizing the defect contrast relative to the background. Thus, potential surface defects are detected by the light reflected back to and captured by the imaging device 24. Since the surface roughness of the paint is highly non-repeatable and varies from surface to surface on a vehicle body (e.g., it being generally higher on a vertical surface than on a horizontal surface), the anomaly detection subsystem 28 provides an adaptive technique that de-emphasizes the image distortions caused by the surface roughness of the paint.

If the surface of the workpiece is painted with a high reflectivity color (e.g., white paint), then the intensity of the light source 22 may saturate the surface of the workpiece such that the imaging device 24 is unable detect surface defects from the reflected light. One skilled in the art will readily recognize that the surface inspection system 10 is operative to dim or brighten the light sources 22 based on the color of the inspected surface. The intensity of the light source is determined through empirical testing for each color of the inspected surface which may be inspected by the surface inspection surface 10.

In operation, the workpiece 25 is coupled to a movable member 26 which translates the workpiece 25 in relation to the light sources 22. More specifically, the movable member 26 travels in a direction substantially perpendicular to the lines of light from the light sources 22. As a result, the inspection surface of the workpiece passes through the lines of light such that the imaging device 24 is able to capture image data representative of a portion of the surface of the workpiece. In addition, the movable member 26 may travel at varying rates of speed. As will be apparent to one skilled in the art, the rate of speed may be adjusted so that the imaging device 24 is able to capture more or less image data for a particular portion of the workpiece as it moves through the lines of light from the light sources 22. Although a conveyor system is presently preferred for use as the movable member 26, this is not intended as a limitation of the broader aspects of the present invention. On the contrary, other types of movable members may be used in conjunction with the present invention.

An anomaly detection subsystem 28 and a defect tracking subsystem 30 reside on one or more of the computing devices (not shown) associated with the surface inspection system 10. As will be more fully explained below, the anomaly detection subsystem 28 is adapted to receive image data from the imaging device 24 and operative to identify potential surface defects in the image data; whereas the defect tracking subsystem 30 is operative to track the potential surface defects, thereby assessing if any one potential surface defect constitutes a defect in the surface of the workpiece. One skilled in the art will readily recognize that the anomaly detection subsystem 28 and the defect tracking subsystem 30 may be implemented using commercially available hardware and software components such as those available from Matrox Electronics Systems Ltd.

A more detailed description of a preferred embodiment of the surface inspection system 10 is provided in relation to FIGS. 3–6. In order to identify potential surface defects, numerous sets of image data are received and processed by the anomaly detection subsystem 28. For instance, a first set of image data 32 and a second set of image data 34 are received by the anomaly detection subsystem 28 in FIG. 3A. Various image processing techniques are then applied to each pair of image frames.

First, an absolute subtraction 36 occurs between the first image frame 32 and the second image frame 34. This operation removes background noise from the imaged surface that are stationary relative to the imaging device. The resulting image frame 38 is indicative of the differences between the two sets of image data. Absolute subtraction is preferred because it enhances all of the anomalies encapsulated in both sets of image data.

Next, the resulting image frame 38 undergoes a thresholding function 40. This operation reduces noise resulting from the subtraction operation. Moreover, the thresholding function 40 converts the integer representation of the image data into a binary representation of the image data. In other words, rather than representing the pixel data as an integer between 0 and 255, the pixel data is stored as either a 0 or 1. This conversion to a binary image frame reduces the data by eight fold, and thus increases the speed of the remaining image processing operations. The resulting binary image frame is shown at 42.

"Orange peel" is randomly varying structure noise that exists on a painted surface. "Orange peel" is part of any painting process on a metal surface and is caused by the viscosity of the paint. Rather than softening the sharp edges of the lines of light from the light sources to minimize the effects of "orange peel" in the image data, the anomaly detection subsystem 28 further includes a filtering process for removing the "orange peel" anomalies found in the image data. As will be apparent to one skilled in the art, this filtering process is particularly applicable to painted inspection surfaces, whereas the remainder of the present invention applies to any bare metal inspection surfaces.

Figure 3A:
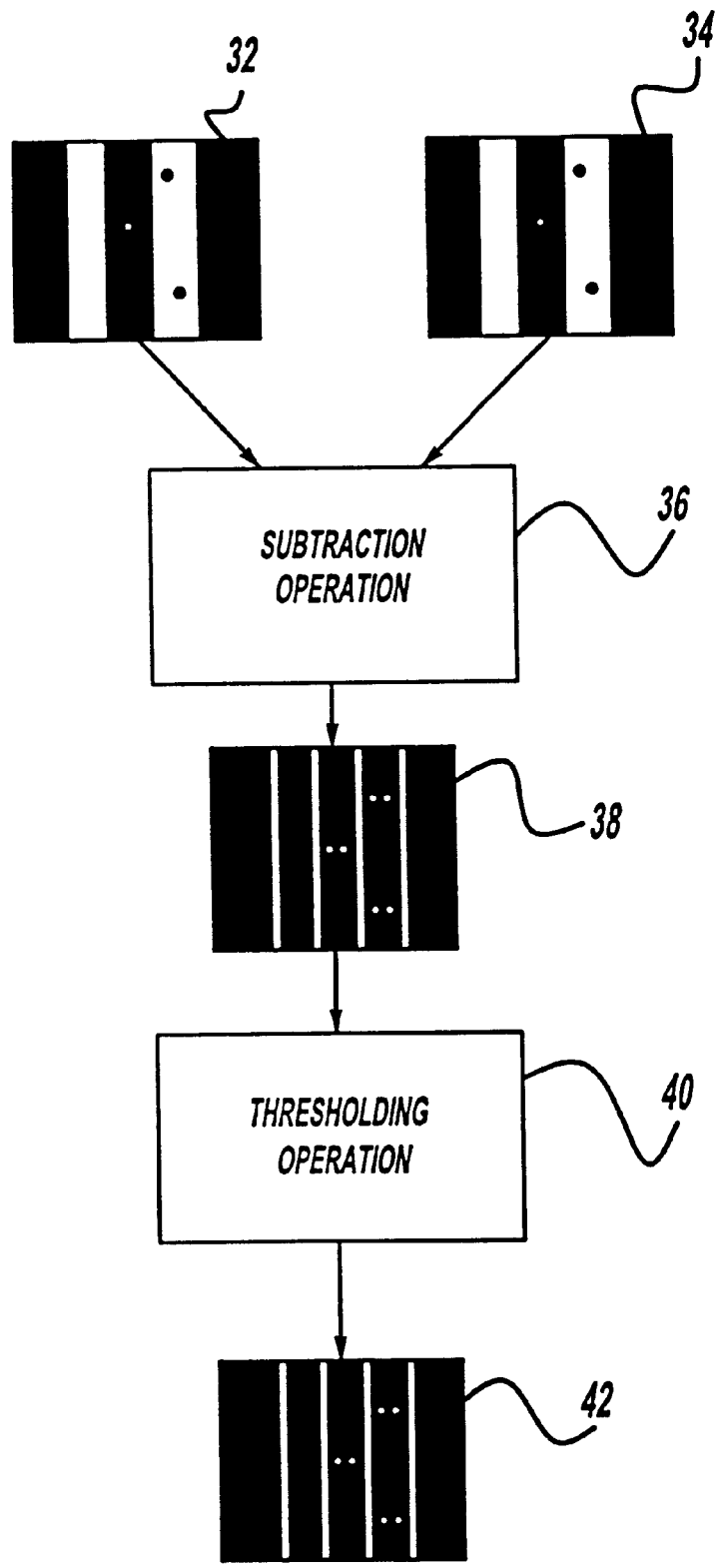
FIGS. 3A–3B illustrates image processing operations which are applied by the anomaly detection subsystem of the present invention.
Figure 3B:
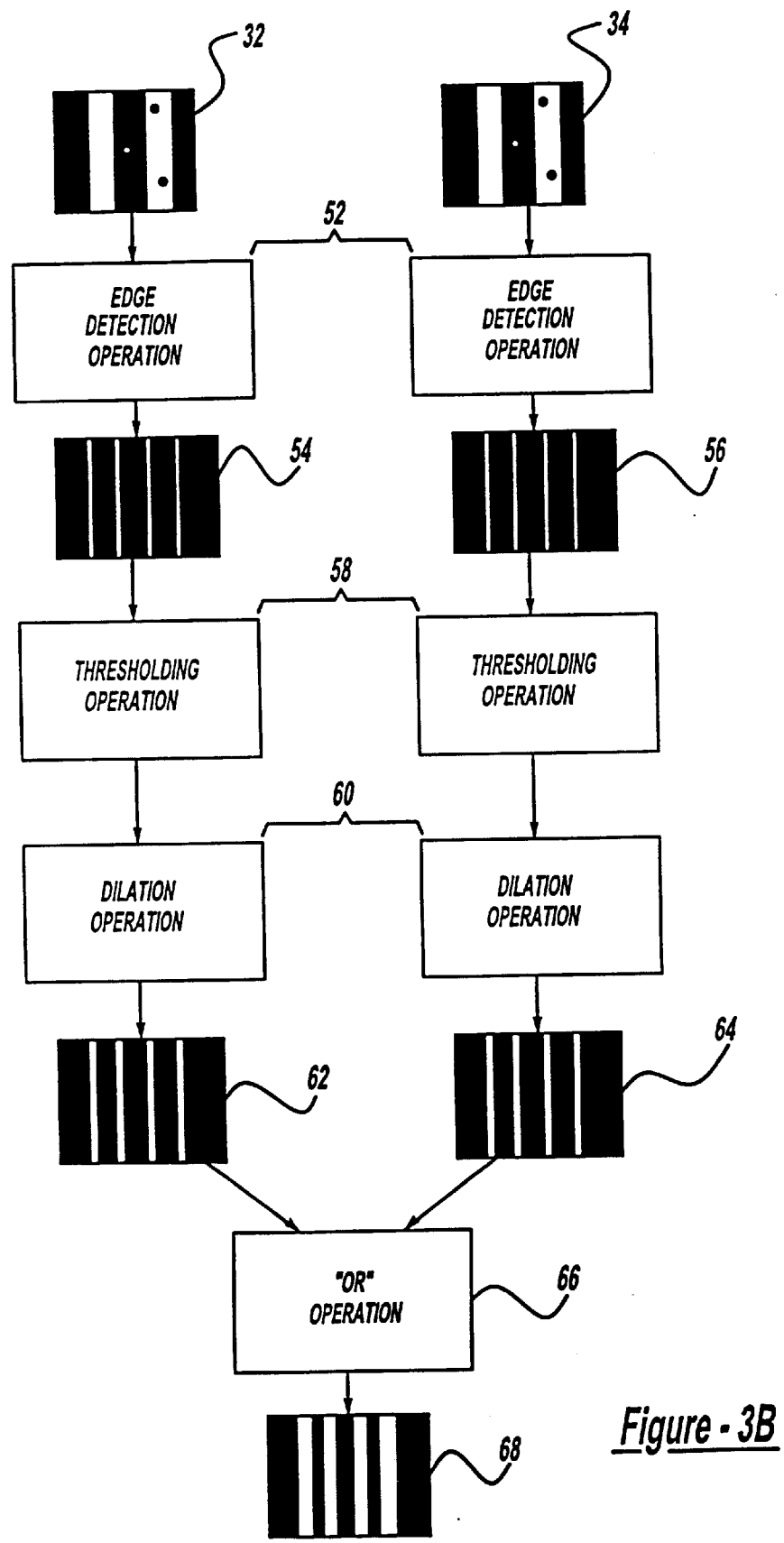

The "orange peel" filtering process begins with a copy of the first set of image data 32 and the second set of image data 34 as shown in FIG. 3B. First, an edge detection operation 52 as is well known in the art is used to identify the edges of the lines of light in each set of image data. The resulting images are shown at 54 and 56. As previously explained, a thresholding function 58 is applied to each of these images 54 and 56 to reduce noise as well reduce the amount of image data. As will be apparent to one skilled in the art, the selection of thresholding is such that the resultant image from step 58 contains predominantly light edges, but not defects that are farther from the edges of the lines of light.

Next, the binary image data frames are dilated using a dilation operation 60 as is well known in the art. In this case, the dilation operation enhances the thickness of the detected edges of the lines of lights. The dilated images are shown at 62 and 64. Each of the above operations are performed on both sets of image data as shown in FIG. 3B. Each set of image data 62 and 64 are combined using an OR operation. The "OR" operation 66 ensures that the "orange peel" anomalies from each set of image data are represented in the resulting composite image data. The resulting composite image data is shown at 68.

Figure 3C:
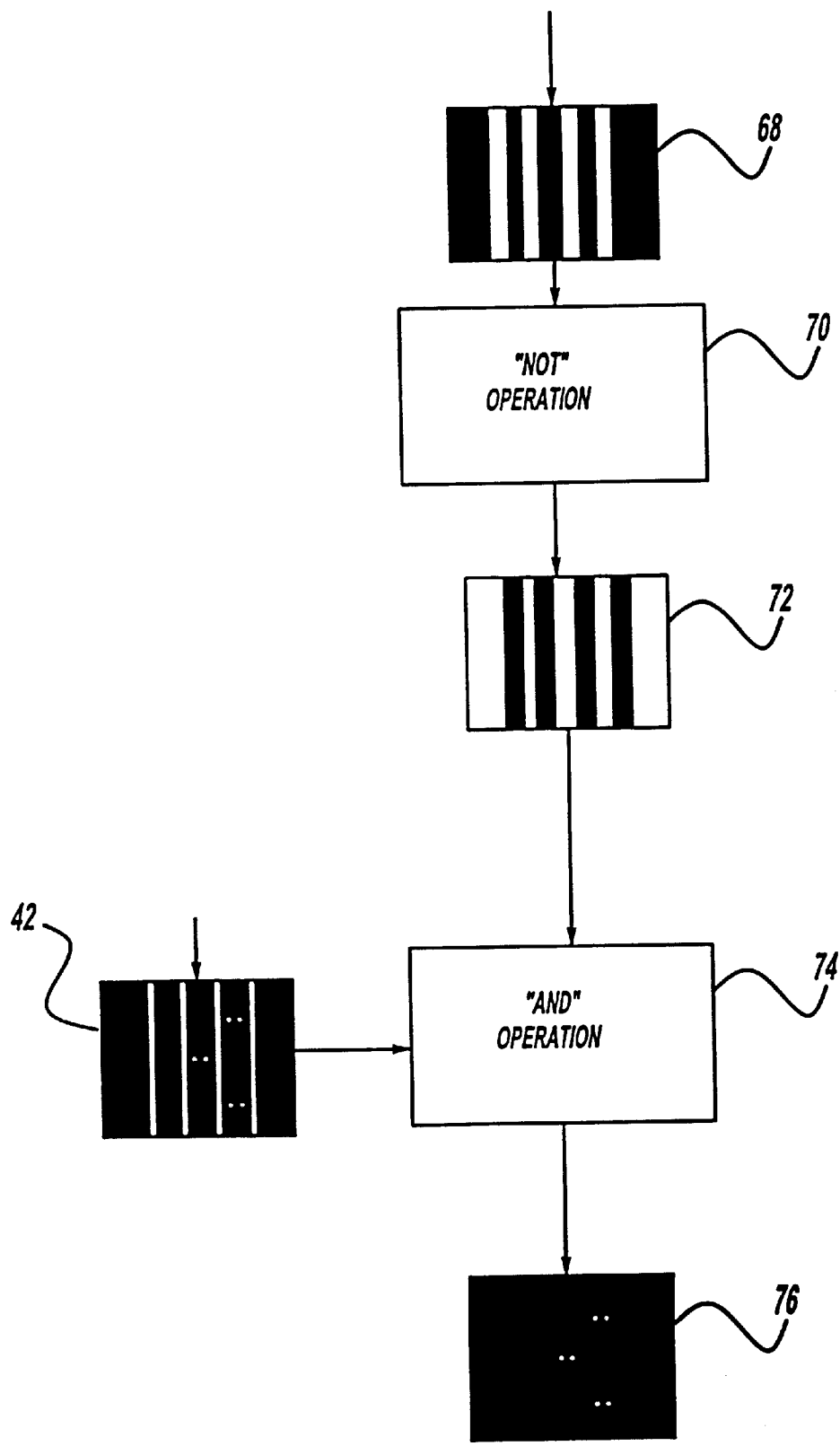

Referring to FIG. 3C, this composite image data 68 is inverted (using a "NOT" operation) 70 to generate an orange peel mask 72. The orange peel mask 72 predominantly represents the "orange peel" on the painted surface of the workpiece and can be applied as a filter to the binary image frame 42. To do so, the orange peel mask 72 is combined with the binary image frame 42 using an "AND" operation 74. In this way, the "orange peel" is removed from the image data. The resultant image frame 76 identifies only potential surface defects in the workpiece and can be used as input to the defect tracking subsystem 30.

Generally, the defect tracking subsystem 30 receives potential surface defect information from the anomaly detection subsystem 18 and tracks the position of each potential surface defect as it moves within the reference frame of the imaging device. If the position of the potential surface defect is accurately predicted, then the potential defect may be classified as a defect in the surface of the workpiece. On the other hand, if the position of the potential surface defect is not accurately predicted, then it may be assumed that the potential defect constitutes random noise and may be disregarded.

In order to track a potential surface defect from frame to frame, the defect tracking subsystem 30 requires at least two resulting image frames from the anomaly detection subsystem 18. As will be more fully described below, a first resulting image frame will yield potential surface defects which were captured in the second set of image data and a second resulting image frame will yield potential surface defects which were captured in a third set of image data. As will be apparent to one skilled in the art, the second set of image data and the third set of image data serve as input to the anomaly detection subsystem 18, thereby resulting in the second resultant image frame received from the anomaly detection subsystem 18. A more detailed description of the defect tracking subsystem 30 is provided in relation to FIGS. 4A and 4B.

First, a dilation operation 94 as is well known in the art is applied to a first resultant image frame received from the anomaly detection subsystem 28. In this case, the dilation operation merges anomalies that are within close proximity of each other (e.g., within a couple of pixels). As a result, the image processing associated with a subsequent connectivity operation is reduced.

The image frame is then overlaid with a grid 96 which divides the larger anomalies into smaller anomalies. For instance, a 30×30 pixel grid may be used to divide up the larger anomalies. As will be more fully explained below, this operation helps to accurately predict the state of a vector that represents the anomaly (which would otherwise be very sensitive to defect shape changes) and to accurately identify certain structural features (e.g., a door handle on a side body panel) on the vehicle body.

The amount of potential surface defect data is further reduced through the use of a connectivity or "blobbing" operation 98. Rather than processing a collection of individual pixel data, the connectivity operation forms shaped objects from the related anomaly pixels. To do so, this operation connects pixels that are similar and within one pixel distance from each other. The connectivity operation is performed within the 30×30 pixel grid. If a "blob" extends outside the grid, then it becomes multiple blobs.

Since the image frame received from the anomaly detection subsystem 28 encapsulates image data from two different image frames, each potential surface defect appears twice in the image frame received from the anomaly detection subsystem 18. A pair elimination operation 100 is therefore used to eliminate half of each paired blobs. To do so, a polarity check is applied to each set of blobs to eliminate at least one of the blobs. For instance, a bounding box is drawn around each of the blobs. The gray level deviation within the bounding box is computed for the most recent image frame and the previous image frame. If the deviation from the latest image frame is greater than the deviation in the previous image frame (and some predefined value), then the blob is determined to be from the latest image frame. Lastly, the blob from the latest image frame is retained whereas the blob from the previous image frame is discarded. Accordingly, each remaining blob corresponds to potential surface defects which were captured in the second set of image data 34 received by the anomaly detection subsystem 18.

Next, a centroid is calculated 102 for each remaining blob. The centroid will be used by the tracking operation 106 to predict the position of the potential surface defect from frame to frame. In addition, a compactness factor (i.e., area/perimeter$^2$) is computed for each blob. Thus, the compactness factor describes the shape of the blob. Each blob may be characterized by a state vector, where the state vector is defined as a list of normalized attributes that describe the location and shape of an anomaly. It is envisioned that other morphological features (e.g., perimeter, area, a region of interest, etc.) may also be computed and used as attributes to defined the state vector for each blob. The normalization is necessary because the information associated with location would have a different range compared with the information associated with the shape. These normalized set of values for location and shape attributes describe each blob. A state vector for each blob in the image frame is then passed along to the tracking operation 106.

Figure 4A:
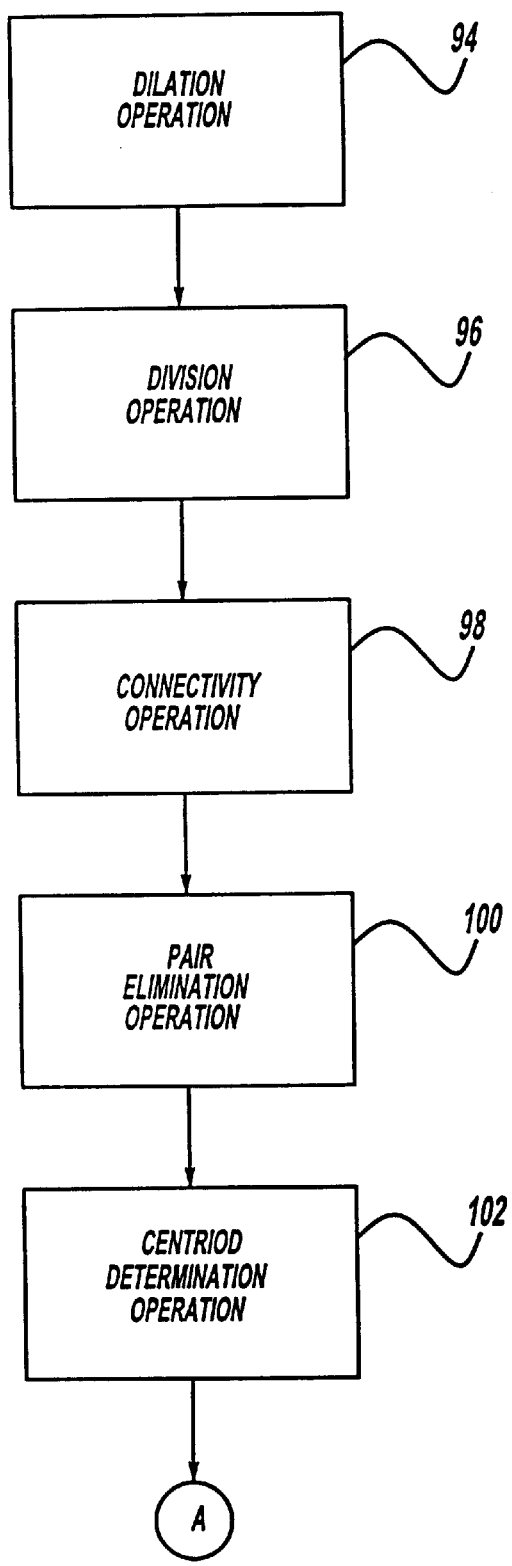
FIGS. 4A and 4B are block diagrams illustrating the operations performed by the defect tracking subsystem in accordance with the present invention.
Figure 4B:
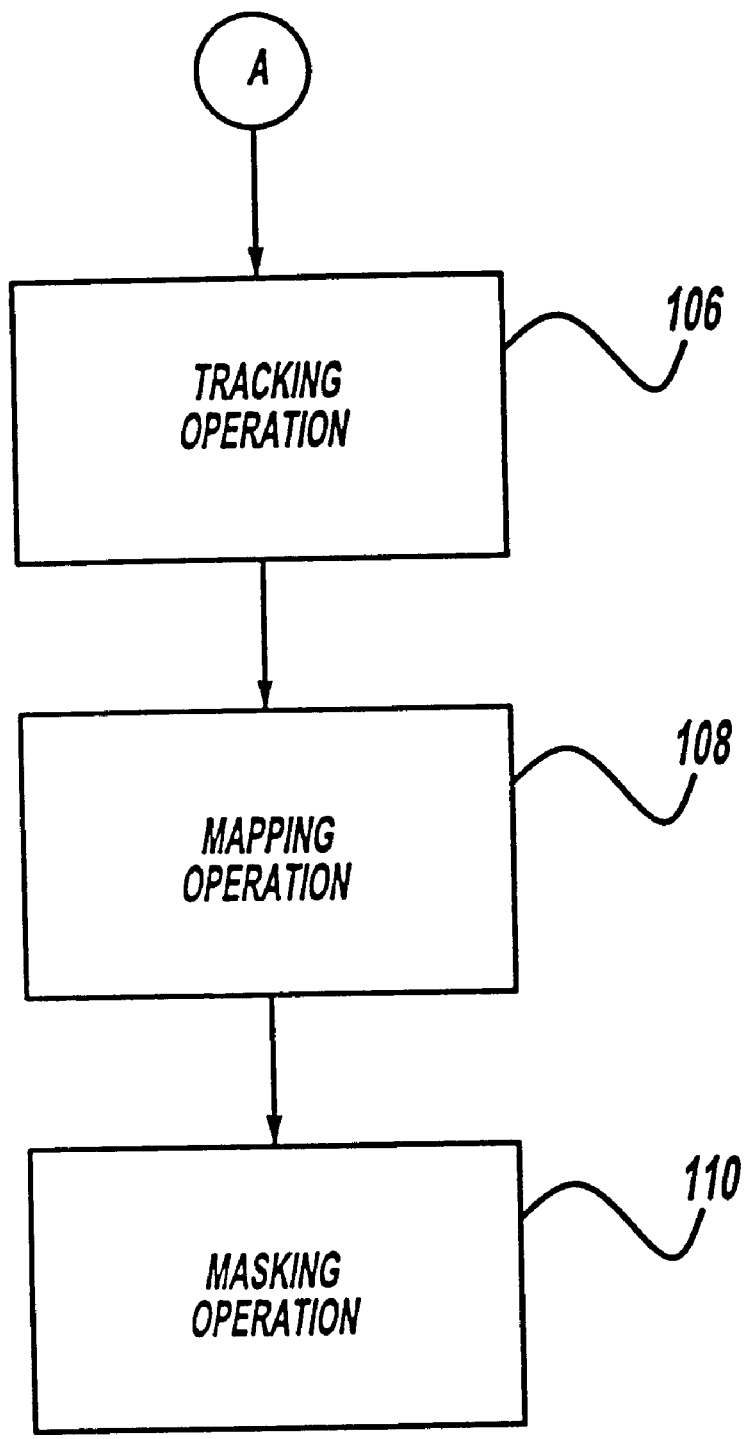

Referring to FIG. 4B, the tracking operation 106 receives a state vector for each blob and tracks the state of each vector as it moves within the reference frame of the imaging device. The match between the predicted state vector and its "true" state is quantified by the probability of both being the same. Since the geometric configuration for each blob is relatively invariant between frames, the compactness factor is used to identify a blob from one frame to the next frame. The centroid for each blob is then used track the location of a blob from frame to frame, thereby determining a predicted location probability for the blob.

In order to predict the position of the potential surface defect, the tracking operation 106 must first compute the velocity at which the defect is travelling in relation to the imaging device. For instance, if the inspection surface of the workpiece is substantially planar, then the potential surface defect is travelling at the same rate (in relation to the imaging device) as the workpiece is being moved by the conveyor system. Since the workpiece is being moved by the conveyor system at a known constant velocity, the position of or distance traveled by the potential surface defect can be predicted from frame to frame. As will be apparent to one skilled in the art, the time occurring between frames is known because the imaging device is capturing image data at a known frequency.

Figure 5:
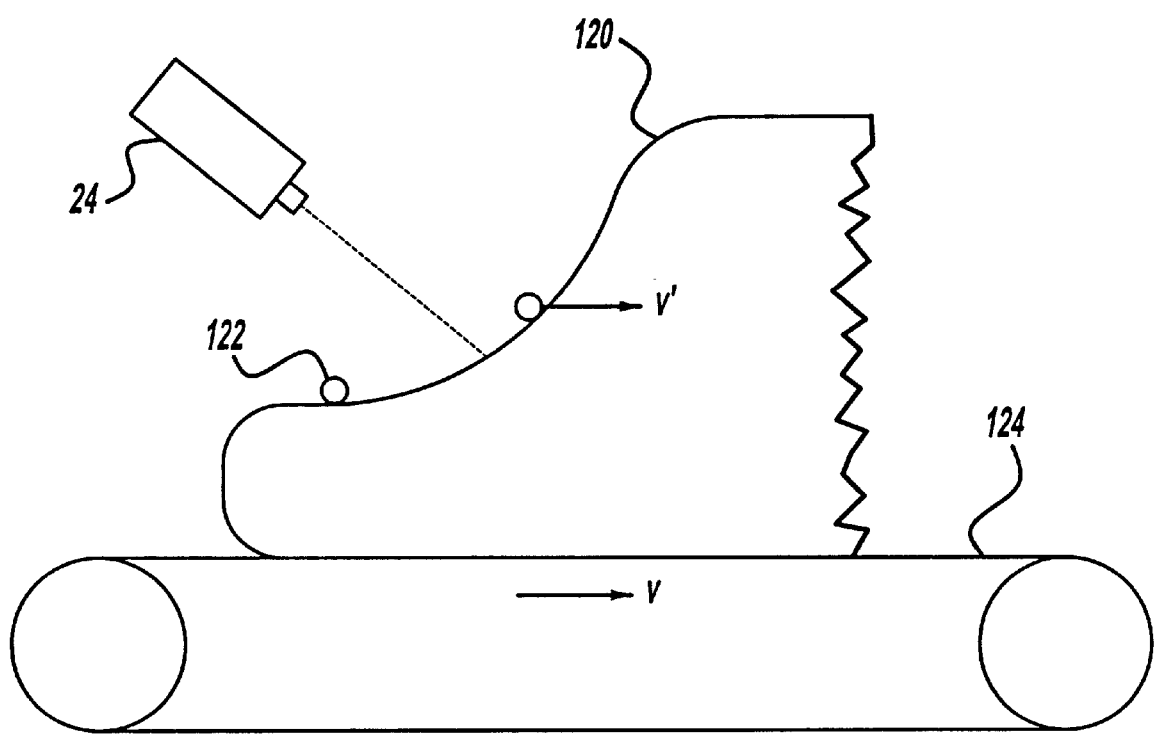
FIG. 5 is a diagram showing how the velocity of a potential surface defect in relation to the imaging device varies from the velocity of the conveyor system.

However, for an inspection surface which is not substantially planar, the rate at which the potential surface is travelling in relation to the imaging device does not correspond to the velocity of the conveyor system. Due to the contour of the inspection surface 120, a potential surface defect 122 will appear to be moving faster (or slower) than the rate of the conveyor system 124 as shown in FIG. 5. Therefore, the defect tracking subsystem 30 utilizes model data indicative of the spatial relationship between the inspection surface of the workpiece and the observation plane of the imaging device in order to determine the velocity of the potential surface defect in relation to the imaging device.

Figure 6:
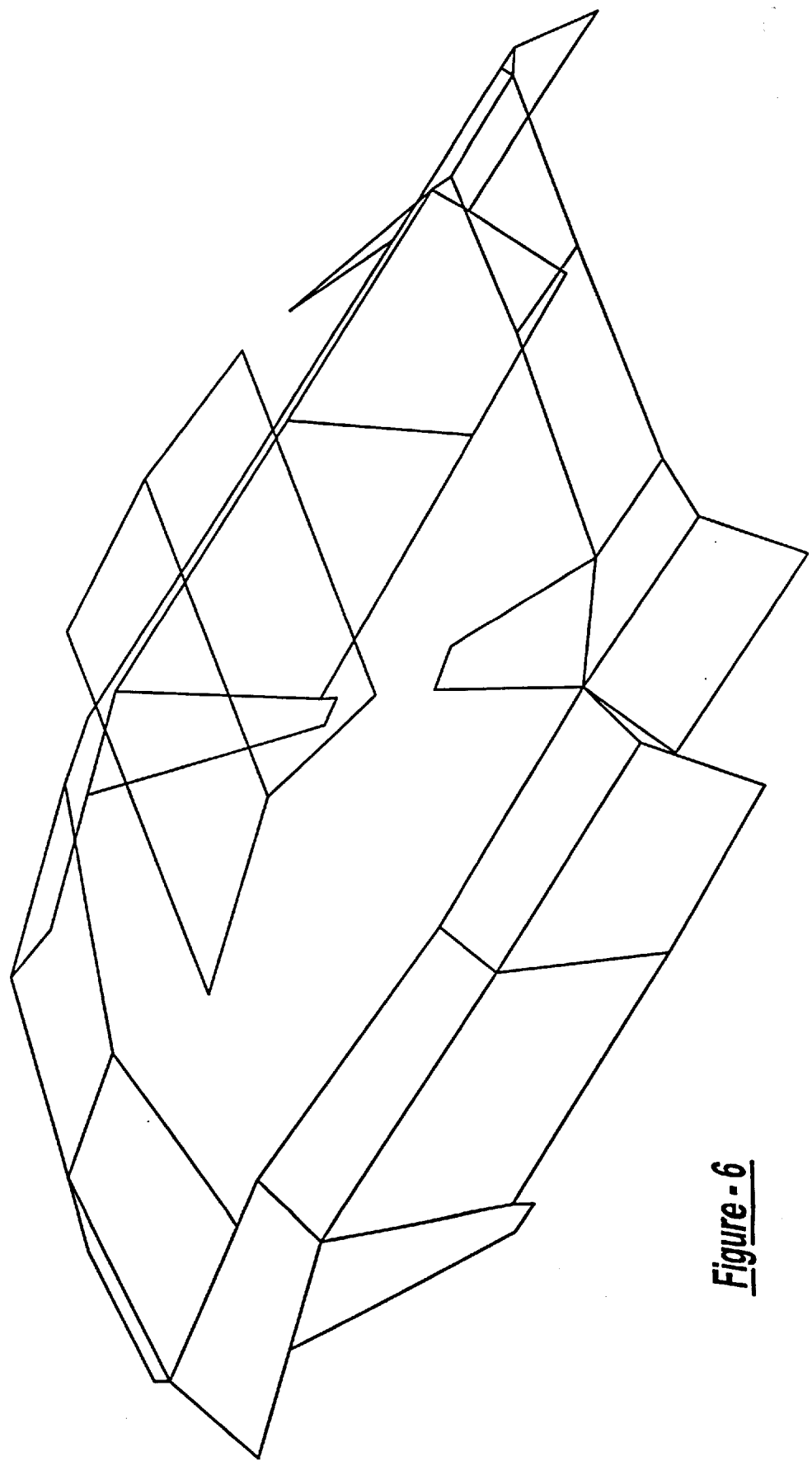
FIG. 6 illustrates an exemplary 3D facet model for an automotive vehicle body in accordance with the present invention.

A CAD model of an automotive vehicle body provides the spatial relationship between the inspection surface of the workpiece and the observation plane of the imaging device. A typical CAD model of a vehicle body is constructed using 5,000 to 10,000 facets. For purposes of the present invention, the vehicle body 130 is modeled using approximately 30 facets as shown in FIG. 6. Although the invention is not limited to a simplified model of the vehicle body, it is readily understood that a 30 facet model provides an adequate approximation of the vehicle body as well as translates into a manageable amount of model data. Model data for each facet is then used to determine the spatial relationship between the observation plane of the imaging device and the inspection surface of the workpiece.

As the workpiece passes through the observation plane of the imaging device, the tracking operation 106 accesses the model data for the facet which corresponds to the portion of the surface being inspected by the inspection system 10. In this way, the tracking operation 106 is able to transform the velocity of the workpiece into a velocity at which the potential surface defect is travelling in relation to the imaging device. The tracking operation 106 then uses this velocity to predict the pixel position of the potential surface defect from frame to frame. Depending on the accuracy of this prediction, the tracking operation 106 assesses whether a potential surface defect constitutes a defect in the surface of the workpiece.

Of course, this velocity transformation process must be done when the inspection surface corresponds to a new facet on the vehicle body. It is further envisioned that the surface inspection system 10 is operative to access different model data for different types of vehicle bodies. In addition, the frequency of the imaging device may be synchronized with the velocity of the conveyor system, thereby further simplifying the velocity transformation process.

Figure 7:
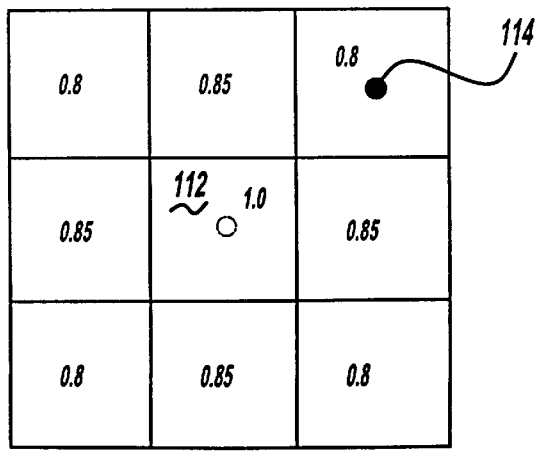
FIG. 7 is a diagram showing an exemplary numeric assignment for each pixel location near the predicted pixel for a potential surface defect which is then used to determine a tracking strength for that potential surface defect in accordance with the present invention.

To assess what constitutes a defect, the tracking operation 106 computes a tracking strength for each potential surface defect as it moves between image frames. The tracking strength is based on the actual location of the potential surface defect relative to the predicted location for that potential surface defect and the similarity in compactness between the state vectors representing the potential surface defects. FIG. 7 illustrates how a numeric value is assigned to each pixel in close proximity of the pixel 112 which corresponds to the predicted location of the potential surface defect. If the actual location of the potential surface defect 114 falls within one of these pixels, then that numeric value is used as a basis for the tracking strength. Because any particular potential surface defect may occur in three or more image frames, the tracking operation further maintains a cumulative tracking strength value for each potential surface defect. This cumulative tracking strength value can then be compared to some predetermined threshold value. It is envisioned that the threshold value is based on the number of times the position for any one potential surface defect was predicted within the viewing area of the imaging device. Finally, each potential surface defect can be classified as a surface defect or not based on whether its cumulative tracking strength exceeds the threshold value. A surface defect may also be characterized based on its cumulative tracking strength and/or the number of observations within the viewing area of the imaging device.

Figure 8:
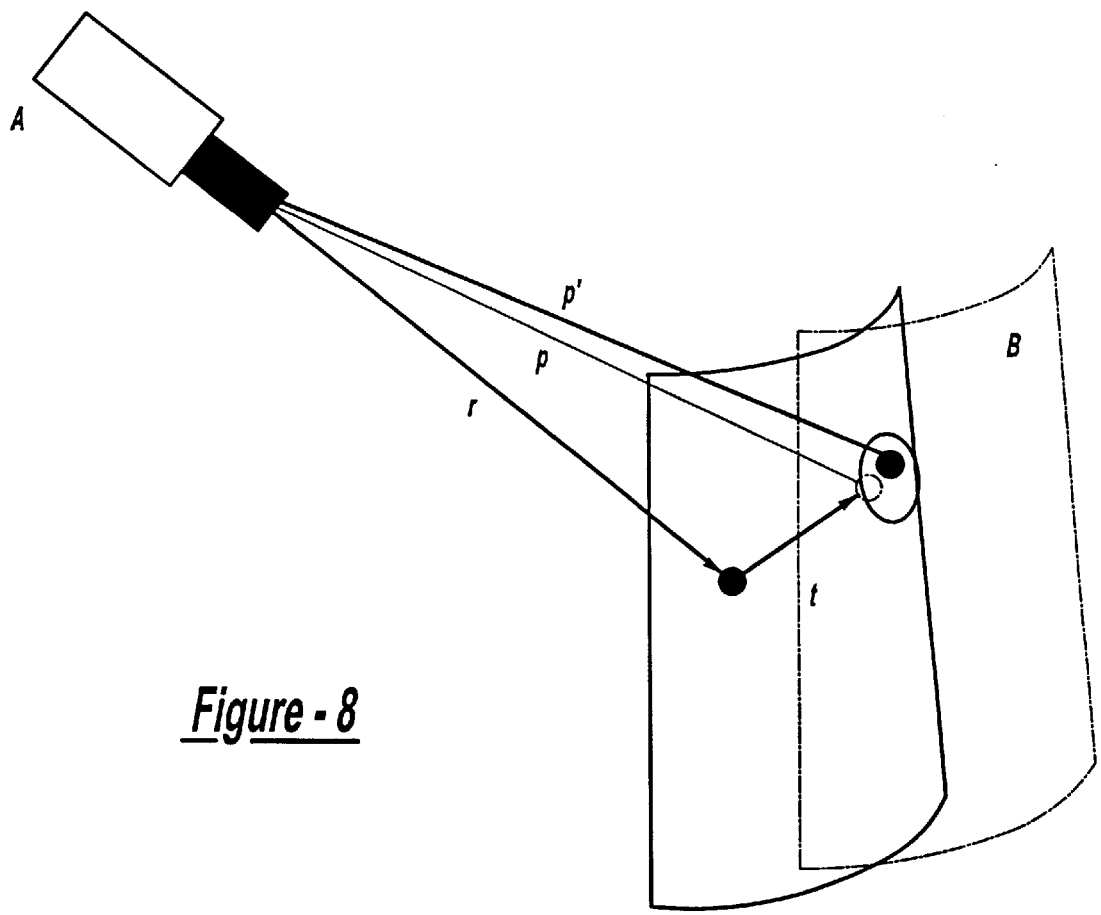
FIG. 8 is a diagram illustrating how identified surface defects are mapped back to a model of the vehicle body in accordance with the present invention.

Returning to FIG. 4B, the defect tracking subsystem 30 includes at least two additional post-processing operations. First, a mapping operation 108 as is well known in the art can be used to map any identified surface defects back onto a model of the vehicle body. A camera model provides a numerical formulation that enables accurate description in the physical world of a pixel on the imaging device. In this case, the camera model incorporates the physical principles that dictate the formation of an image in the imaging device. Using this camera model, a ray is drawn through a potential surface defect such that it passes through a surface on the vehicle body as shown in FIG. 8.

Model data for each facet is translated along with the vehicle body. This translation is dictated by the measurement of position of the vehicle body. Intersection of this ray with a facet provides the location of the defect on the vehicle body. A vector summation of this ray with the translation vector associated with a facet on the vehicle body provides a method for accurately predicting the position of the defect after car translation. Again, the camera model is used to calculate the position of the defect in the image after translation. The accuracy of the prediction depends on the accuracy of the facet model data and thus the translation vector. It should be noted that a velocity calculated using the above procedure is not limited to a single direction of travel for a surface defect along a non-planar surface of the vehicle body. Identified surface defects can also be displayed on a CRT or other type of display device which is associated with the computing device 18 of the surface inspection system 10.

A masking operation 110 is then used to filter out any known structural features of the vehicle body. In this case, since the structural features (e.g., a door handle on a side body panel) are identified as surface defects by the surface inspection system, the masking operation 110 ensures that these features are not misidentified as surface defects.

While the invention has been described in its presently preferred form, it will be understood that the invention is capable of modification without departing from the spirit of the invention as set forth in the appended claims.

What is claimed is:

1. A surface inspection system for detecting defects on a surface of a workpiece, comprising:

a diffused light source for emitting an elongated line of light onto the surface of the workpiece;

a movable member for translating the workpiece in relation to said light source;

an imaging device for capturing two or more sets of image data representative of a portion of the surface of the workpiece, said imaging device having a field of observation and being positionable at a vantage point such that the line of light is within the field of observation;

a data structure for storing model data indicative of a spatial relationship between said portion of the surface of the workpiece and the observation plane of said imaging device and;

an anomaly detection subsystem adapted to receive at least a first set of image data and a second set of image data from said imaging device, said anomaly detection module identifying at least one potential surface defect in said first set of image data and said second set of image data; and a tracking subsystem connected to said data structure and said anomaly detection module for tracking the potential surface defect from said first set of image data to said second set of image data using said model data, thereby assessing if the potential surface defect constitutes a defect in the surface of the workpiece.

2. The surface inspection system of claim 1 wherein said tracking subsystem operative to transform the velocity of the workpiece into a velocity at which a potential surface defect is moving in relation to said imaging device through the use of said model data, and to predict a location of the potential surface defect from said first set of image data to said second set of image data through the use of said velocity.

3. The surface inspection system of claim 1 wherein the workpiece is modeled using a plurality of facets, where each facet represents a portion of the surface of the workpiece, and said model data is indicative of the spatial relationship between each facet of the workpiece and the observation plane of said imaging device.

4. The surface inspection system of claim 3 wherein said tracking subsystem operative to access model data which corresponds to the portion of the surface of the workpiece being inspected by the surface inspection system.

5. The surface inspection system of claim 1 further comprising at least two diffused light sources for emitting at least two elongated lines of light onto the surface of the workpiece.

6. The surface inspection system of claim 5 being operative to adjust an intensity of said light sources based on the color of the surface of the workpiece.

7. The surface inspection system of claim 1 wherein said anomaly detection subsystem includes:

a subtraction module receiving said first set of image data and said second set of image data and operative to generate image data indicative of the differences between said first set of image data and said second set of image data; and a thresholding module receiving the image data from said subtraction module and operative to generate a binary representation of said image data.

8. The surface inspection system of claim 1 wherein said anomaly detection subsystem further includes:

a edge detection module receiving said first set of image data and said second set of image data and operative to identify the edges of the line of light in each set of image data;

a second thresholding module receiving said first and second sets of image data from said edge detection module and operative to generate a binary representation for each set of image data;

a dilation module receiving said first and second sets of image data from said second thresholding module and operative to thicken the edges of the line of light in each set of image data; and a mask formation module receiving said first and second sets of image data from said dilation module, said mask formation module operative to combine said first set of image data with said second set of image data into a resultant set of image data using an OR operation and to invert the resultant image data using a NOT operation, thereby forming a mask for filtering out a portion of the noise in the image data.

9. The surface inspection system of claim 1 wherein said anomaly detection subsystem further includes:

an anomaly identification module receiving image data from said thresholding module and a mask from said mask formation module and operative to apply said mask to said image data using an AND operation, thereby filtering out a portion of the noise in the image data.

10. The surface inspection system of claim 1 wherein said movable member is further defined as a conveyor system.

11. The surface inspection system of claim 1 wherein said workpiece is further defined as a vehicle body for a motor vehicle and the surface inspection system operates within a motor vehicle manufacturing system.

12. A method of detecting defects in a surface of a workpiece using a surface inspection system, comprising the steps of:

emitting a line of light onto the surface of the workpiece;

passing the surface of the workpiece through the line of light;

capturing a first set of image data representative of a portion of the surface of the workpiece using an imaging device, said imaging device having a plane of observation and being positionable at a vantage point such that the line of light is within its plane of observation;

providing model data indicative of the spatial relationship between said portion of the surface of the workpiece and the observation plane of said imaging device;

capturing a second set of image data representative of said portion of the surface of the workpiece using said imaging device;

identifying at least one potential surface defect in said second set of image data;

capturing a third set of image data representative of said portion of the surface of the workpiece using said imaging device; and tracking the potential surface defect from said second set of image data to said third set of image data using said model data, thereby assessing if the potential surface defect constitutes a defect in the surface of the workpiece.

13. The method of claim 12 wherein the step of emitting an elongated line of light further comprises using at least two diffused light sources to emit at least two elongated lines of light onto the surface of the workpiece.

14. The method of claim 13 further comprising the step of adjusting an intensity of said light sources based on the color of the surface of the workpiece.

15. The method of claim 12 wherein the step of identifying at least one potential surface defect further comprises:

subtracting said first set of image data from said second set of image data to form an intermediary set of image data, the intermediary set of image data indicative of potential surface defects in at least said second set of image data.

16. The method of claim 15 further comprises generating a binary representation of the intermediary set of image data.

17. The method of claim 15 further comprises the step of filtering out at least a portion of noise in said first and second set of image data, where the noise is caused by a variation in the viscosity of the paint on the surface of the workpiece.

18. The method of claim 17 wherein the step of filtering out at least a portion of noise further comprises:
providing a copy of said first set and said second set of image data;
identifying the edges of the line of light in each copy of image data;
combining the copy of said first set of image data with the copy of said second set of image data into a resultant set of image data by using an OR operation;
inverting said resultant set of image data using a NOT operation, thereby forming a mask for filtering out a portion of the noise; and
applying said mask to said intermediary set of image data using an AND operation, thereby filtering out a portion of the noise in the image data.

19. The method of claim 12 further comprising:
modeling the workpiece using a plurality of facets, where each facet represents a portion of the surface of the workpiece;
providing model data indicative of the spatial relationship between each facet of the workpiece and the observation plane of said imaging device; and
tracking the potential surface defect using model data which corresponds to the portion of the surface of the workpiece being inspected by the surface inspection system.

20. The method of claim 12 wherein the step of tracking the potential surface defect further comprises:
determining a first location of the potential surface defect in a reference frame for said imaging device, where the first location derived from said second set of image data;
determining a velocity for the workpiece;
transforming the velocity of the workpiece into a velocity at which potential surface defects are moving in relation to the said imaging device through the use of said model data;
predicting a location of the potential surface defect in said third set of image data by using the velocity for potential surface defects;
determining a second location of the potential surface defect in the reference frame of said imaging device, where the second location is derived from said third set of image data; and
comparing the predicted location of the potential surface defect with said second location of the potential surface defect, thereby tracking the potential surface defect.

21. A method of detecting defects in a surface of a workpiece, comprising the steps of:
emitting a line of light onto the surface of the workpiece;
passing the surface of the workpiece through the line of light;
capturing a first set of image data representative of a portion of the surface of the workpiece using an imaging device, said imaging device having a plane of observation and being positionable at a vantage point such that the line of light is within its plane of observation;
identifying at least one potential surface defect in said first set of image data;
determining a velocity for the workpiece;
transforming the velocity of the workpiece into a velocity at which potential surface defects are moving in relation to said imaging device;
capturing a second set of image data representative of said portion of the surface of the workpiece using said imaging device; and
tracking the potential surface defect from said first set of image data to said second set of image data using the velocity at which potential surface defects are moving in relation to said imaging device, thereby assessing if the potential surface defect constitutes a defect in the surface of the workpiece.

22. The method of claim 21 wherein the step of emitting an elongated line of light further comprises using at least two diffused light sources to emit at least two elongated lines of light onto the surface of the workpiece.

23. The method of claim 22 further comprising the step of adjusting an intensity of said light sources based on the color of the surface of the workpiece.

24. The method of claim 21 wherein the step of identifying at least one potential surface defect further comprises:
subtracting said first set of image data from said second set of image data to form an intermediary set of image data, the intermediary set of image data indicative of potential surface defects in at least said second set of image data.

25. The method of claim 24 further comprises generating a binary representation of the intermediary set of image data.

26. The method of claim 21 further comprises the step of filtering out at least a portion of noise in said first and second set of image data prior to tracking the potential surface defect, where the noise is caused by a variation in the viscosity of the paint on the surface of the workpiece.

27. The method of claim 26 wherein the step of filtering out at least a portion of noise further comprises:
providing a copy of said first set and said second set of image data;
identifying the edges of the line of light in each copy of image data;
combining the copy of said first set of image data with the copy of said second set of image data into a resultant set of image data by using an OR operation;
inverting said resultant set of image data using a NOT operation, thereby forming a mask for filtering out a portion of the noise; and
applying said mask to said intermediary set of image data using an AND operation, thereby filtering out a portion of the noise in the image data.

28. The method of claim 21 further comprising:
modeling the workpiece using a plurality of facets, where each facet represents a portion of the surface of the workpiece;
providing model data indicative of the spatial relationship between each facet of the workpiece and the observation plane of said imaging device; and
tracking the potential surface defect using model data which corresponds to the portion of the surface of the workpiece being inspected by the surface inspection system.

* * * * *